United States Patent [19]

Jackson

[11] Patent Number: 5,105,656
[45] Date of Patent: Apr. 21, 1992

[54] METHOD AND APPARATUS FOR TESTING POLYMER DRILLING MUD

[76] Inventor: Boyd L. Jackson, 1701 Lavonia, Pasadena, Texas 77502

[21] Appl. No.: 491,003

[22] Filed: Mar. 9, 1990

[51] Int. Cl.$^5$ .......................................... G01N 15/04
[52] U.S. Cl. ................................................ 73/61.4
[58] Field of Search ............ 73/61.4, 38, 153, 863.23; 162/49

[56] References Cited

U.S. PATENT DOCUMENTS

| | | | |
|---|---|---|---|
| 3,216,242 | 11/1965 | Eyerich | 73/38 |
| 4,402,214 | 9/1983 | Morgan et al. | 73/38 |
| 4,517,053 | 5/1985 | Devine | 73/863.23 |
| 4,613,406 | 9/1986 | Gess | 73/61.4 |
| 4,748,849 | 6/1988 | Jamison et al. | 73/61.4 |

Primary Examiner—Hezron E. Williams
Attorney, Agent, or Firm—Harrison & Egbert

[57] ABSTRACT

A test cell utilizing a pressure vessel having a vertically oriented filter having 7 square inches of flow area located therein with the vessel being sufficiently deep to provide a settling chamber below the filter for weighting materials which settle out in the presence of the high temperatures. The methods presented herein provide a means for testing polymer drilling muds that yield consistent and repeatable results that can be correlated to fluid loss indices of other drilling muds. The methods involve filling the vessel with polymer mud, heating the mud to the predetermined temperature, applying pressure to the drilling mud to force it through a 7 square inch flow area filter and measuring the filtrate over a predetermined period of time to establish the flow index.

14 Claims, 1 Drawing Sheet

METHOD AND APPARATUS FOR TESTING POLYMER DRILLING MUD

TECHNICAL FIELD OF THE INVENTION

This invention relates generally to methods and apparatus for testing drilling muds. More particularly, but not by way of limitation, this invention relates to improved testing apparatus and methods useful in testing polymer drilling muds.

BACKGROUND OF THE INVENTION

In an effort to standardize specifications of drilling muds, the American Petroleum Institute has promulgated a series of test procedures and specified test apparatus that are utilized for the purpose of determining the various characteristics of drilling muds. Among these is a mud filtration device that is used for the purpose of providing a fluid loss standard or index for mud. Basically, two tests are used to determine the fluid loss index.

One test is run at room temperature with about 100 psi pressure differential across the filter of the apparatus. The volume of filtrate flowing from the mud through the filter is measured over a predetermined period of time to provide a fluid loss number.

A second test is similar, but run at higher pressure and higher temperature with the pressure differential being approximately 500 psi and the temperature being at the anticipated bottom hole temperature, usually between 250° F. and 400° F. Again, the filtrate from the mud passing through the filter is measured over a predetermined period of time to provide the fluid loss number. In the low temperature apparatus a 7 square inch filter is disposed horizontally at the bottom of the test or pressure vessel through which the filtrate passes, while in the high temperature apparatus a 3½ square inch horizontally disposed filter is used. To correlate the tests, the number derived from the high temperature test is doubled.

The tests have proved to be adequate for the standardization of a fluid loss number or index which provides a comparison between various drilling muds. Recently, the composition of the drilling muds has changed to include new materials that have become available. The new muds are generally referred to as high temperature polymer drilling fluids. The apparent advantage of such muds is that the materials used therein can be standardized. Also, the number of materials used in the mud can be reduced. A discussion of such muds and the testing thereof is available in a paper entitled "The Development of a Deflocculated Polymer Mud for HTHP Drilling" by J. C. Abdon, B. L. Jackson, and G. S. McClellan. The paper was published in 1989 by the Society of Petroleum Engineers under S.P.E. number 17924. The new polymer drilling muds utilize as a viscosifier, a polymer known as xanthan gum. Filtration control is provided in the mud by a polyanionic lignin polymer and deflocculation is provided by an acrylic co-polymer. Weighting is provided by the use of barite.

It was noticed during the standard A.P.I. filtration testing of the polymer muds at the higher temperature that the fluid loss number seemed to vary substantially and it was further noticed that the fluid loss number did not seem to be indicative of what was actually happening in the well. An analysis of the problem, upon recognizing the foregoing contradiction, seemed to indicate that at temperatures above 250° F., and in the presence of oxygen, the xanthan gum oxidized, causing the mud viscosity to drop and permitting weighting materials in the mud to settle out of suspension. Weighting materials may constitute as much as 48 percent by volume of the mud. Such a phenomena appeared to occur in the test cell where oxygen was present, but not in the well where at bottom hole, no oxygen was available for the oxidation process. From this realization, it was determined that the inconsistent results being obtained in the filtration test unit of the American Petroleum Institute standard resulted from the settling out of the weighting materials, such as barite, onto the horizontally positioned filter located at the bottom of the test vessel.

The resulting loss of viscosity promoted the settling of barite. Two phases developed: a barite/liquid phase on the bottom and a liquid/colloid phase above. This upper phase contained a predominant portion of the lignin polymer. When filtration was initiated, the colloids (including the lignin polymer) were filtered out in the upper portion of the barite plug. The result was a limited concentration of lignin polymer in the filter cake and hence a high rate of filtration.

Some of the apparatus and methods utilized for the testing and determination of drilling mud characteristics are contained in U.S. Pat. No. 3,055,208 issued Sept. 25, 1962 to J. P. Gallus; U.S. Pat. No. 3,289,467 issued Dec. 6, 1966 to H. W. Parker et al.; and U.S. Pat. No. 4,538,452 issued Sept. 3, 1985 to Ivan Hrvojic. While none of the foregoing patents illustrate apparatus that is precisely like that proposed herein, various characteristics of the systems discussed are shown in the patents. For example, in Parker U.S. Pat. No. 3,289,467, a vertical filtration system is utilized for determining drilling mud characteristics such as water loss under dynamic conditions.

An object of this invention is to provide improved polymer mud testing apparatus and testing methods that correlate with the long-standing fluid loss standards developed over the years by the American Petroleum Institute.

SUMMARY OF THE INVENTION

In one aspect, this invention provides an improved method of filtration testing polymer drilling muds for fluid loss characteristics that comprises the steps of introducing the mud to be tested into a test vessel having a vertically oriented filter; elevating the temperature of the mud to a predetermined value; allowing weighting material in the mud to settle out of suspension; raising the pressure in the vessel and on the mud to apply a pressure differential of a predetermined value across the filter; and measuring the volume of filtrate from the mud flowing through the filter over a predetermined time period.

In another aspect, this invention provides an improved filtration test vessel for use in the fluid loss testing of polymer drilling muds that comprises a pressure vessel having a generally vertically oriented side wall, a top, and a bottom. The pressure vessel includes a filtrate port intermediate the top and bottom and a port for introducing mud into the pressure vessel. Heating apparatus is provided for elevating the mud temperature and pressure means is provided for raising the pressure of mud in the pressure vessel. A filter is located in the pressure vessel that is generally vertically oriented. The filter has a first side that is exposed to the mud and a second side in communication with the filtrate port and a bottom edge that is located above the bottom of the pressure vessel providing a settling chamber wherein weighting materials in the mud can settle without affecting the flow area through the filter.

BRIEF DESCRIPTION OF THE DRAWINGS

The foregoing and additional objects and advantages of the invention will become more apparent when the following detailed description is read in conjunction with the accompanying drawing wherein like reference characters denote like parts in all views and wherein.

DETAILED DESCRIPTION OF THE PREFERRED EMBODIMENT

Figure 1:
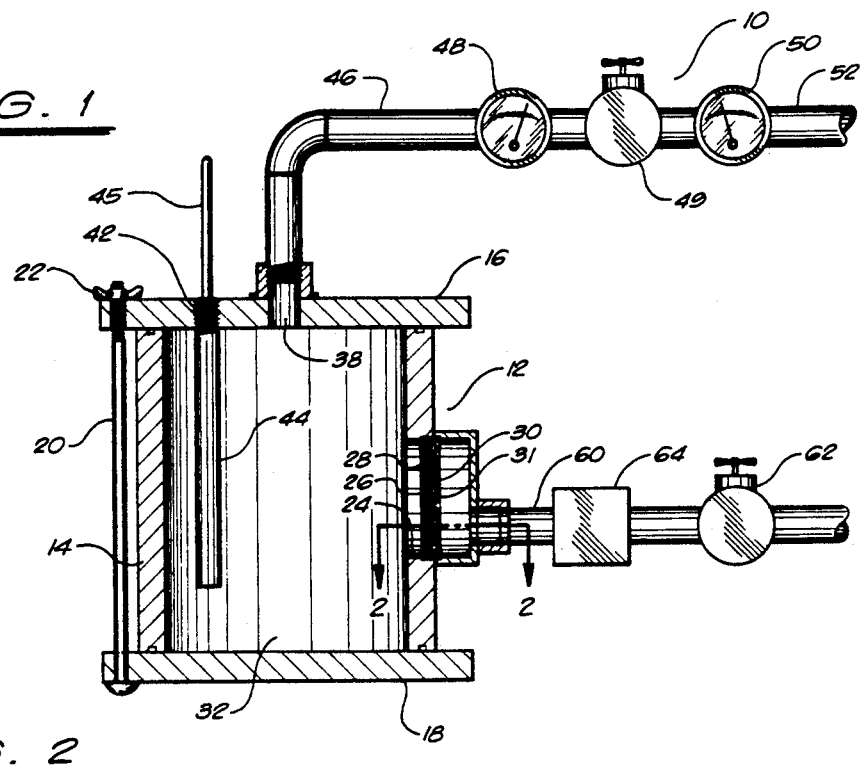
FIG. 1 is a vertical cross section of a pressure vessel that is constructed in accordance with the invention.
Figure 2:
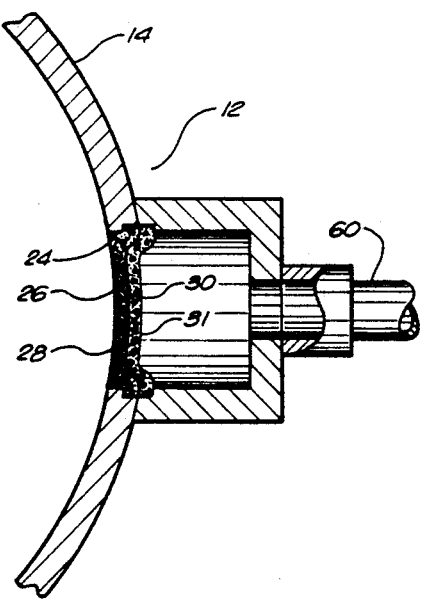
FIG. 2 is a fragmentary cross-sectional view taken generally along the line 2—2 of FIG. 1.

Referring to the drawing and to FIGS. 1 and 2 in particular, shown therein and generally designated by the reference character 10 is apparatus for filtration testing drilling muds and particularly polymer drilling muds that is constructed in accordance with the invention. As shown in FIG. 1, the system 10 includes a test vessel 12 that is designed to withstand at least a pressure differential of 500 psi from the interior to the exterior thereof.

The pressure vessel 12 includes a vertically oriented sidewall 14, a top 16, and a bottom 18. The sidewall 14, top 16 and bottom 18 are held assembled by a plurality of releasable fasteners 20 (only one is shown in FIG. 1). The vessel 12 could be constructed from two members if desired with only the top 16 being a separate member. Quick release fasteners and the like could be used instead of wing nuts 22 which are illustrated as being located on the fasteners 20.

The sidewall 14 is provided with a filtration port 24 that extends therethrough between the top 16 and bottom 18. A filter 26 is mounted as close to flush with the interior of the sidewall 14 as possible. One face 28 of the filter 26 is in communication with the interior of the pressure vessel 12 and the other face 30 is disposed adjacent to the filtration port 24. The filter 26 will be the same material, Whatman 50, with the same fluid flow characteristics as that utilized in the standard A.P.I. test. Also, it should be pointed out that the filter 26 should have a flow area of 7 square inches, which is twice the filter area used in the standard A.P.I. test vessel for the high temperature, high pressure tests. FIG. 2 is a horizontal cross-section taken generally along the line 2—2 of FIG. 1 and through the filtrate port 24 illustrating the flush arrangement of the filter 26 with respect to the filtrate port 24. A backup screen 31 is positioned to support the filter 26.

The lower edge of the filter 26 is located substantially above the bottom 18 of the vessel 12 to form a settling chamber 32. Sufficient volume is to be provided so that weighting materials and other solids settling out of the mud solution does not cover any portion of the flow area of the screen 26.

The top 16 of the pressure vessel 12 includes a pressure port 38. The port 38 is connected in fluid communication with a conduit 40. The port 38 is provided for the purpose of applying pressure to the mud in the pressure vessel 12 as will be described.

The top 16 also includes an opening 42 for receiving a thermowell 44. The vessel 12 is usually heated externally by a heating mantle to elevate the mud temperature. If desired, an internal heating element (not shown) could replace the thermowell 44. Either type heating element can be used so long as it elevates the temperature of the mud in the pressure vessel 12. The upper end of the thermowell 44 is open and receives a thermometer 45 for monitoring the mud temperature.

A conduit 46 extends from the port 38 to a pressure gauge 48, a regulator 49, and to a pressure gauge 50. Conduit 52 connects the vessel 12 to a source of pressurized fluid (not shown). The regulator 49 is used to set the pressure in the vessel 12.

The arrangement is such that the gauge 48 indicates a pressure in the vessel 12, and gauge 50 indicates available pressure. After filling the pressure vessel 12 with mud and replacing the top 16, the source of gas or liquid under pressure (not shown) is connected through the regulator 49 to pressure the mud in the vessel 12.

A conduit 60 is connected to the filtrate port 24 and to a downstream pressure control regulator 62. Interposed between the control regulator 62 and the filtrate port 24 in the conduit 60 is a meter 64 that is utilized to determine the amount of filtrate flowing through the conduit 60 over a predetermined period of time. The predetermined period of time is set in accordance with A.P.I. standards and is usually 30 minutes. If desired, and in a less sophisticated system, the meter 64 can be omitted and the filtrate simply deposited in a beaker or the like.

OPERATION OF THE PREFERRED EMBODIMENT

With the apparatus 10, a filtration test begins with the removal of the top 16 and filling the interior of the vessel 12 with mud. The top 16 is replaced and pressure is applied through the gauge 50, regulator 49 and into the interior of the test vessel 12. The regulators 49 and 62 are adjusted until the differential pressure across the filter 26 is 200 psi.

The vessel 12 is heated so that the temperature of the mud is elevated to anticipated bottom hole temperature in the well where the mud is to be used. Generally, such temperature will be between 250° F. and 400° F.

As the temperature of the polymer mud rises in the test vessel 12, weighting materials, such as barite, may settle out of suspension, and fall into the settling chamber 32 which is formed in the lower end of the pressure vessel 12 below the lowermost end of the filter 26. Due to the vertical orientation of the filter 26, the weighting materials and any other solids setting out do not attach to the filter 26, but rather settle into the settling chamber 32. Accordingly, the filter 26 is clear for filtration purposes.

The pressure in the vessel 12 is regulated by adjusting the regulators 49 and 62 to produce the desired differential of 500 psi. The valve 62 is opened and filtrate flowing through the filter 26 and outwardly through filter 26 is measured by the meter 64 over the predetermined period of time of 30 minutes. A fluid loss index is then recorded for the mud at the particular bottom hole temperature.

Figure 3:
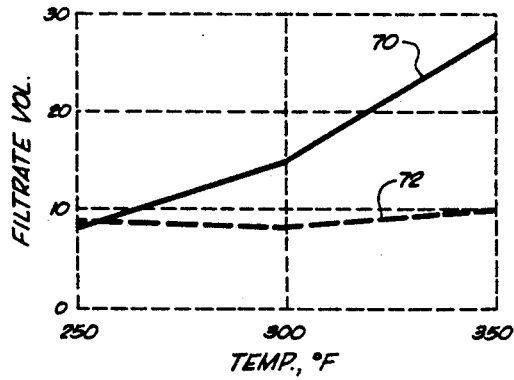
FIG. 3 is a graph illustrating the difference in filtrate volume flowing through the test vessel of FIG. 1 versus the volume of filtrate flowing through a standard A.P.I. test cell.

FIG. 3 is a chart that illustrates the advantages of the filter system 10. As shown on the chart, the curve 70 resulted from the testing of a series of polymer muds in a standard A.P.I. test cell at various temperatures. Curve 72 resulted from the testing of a series of polymer muds at varying temperatures in the filtration test system 10 that was constructed in accordance with this invention. It is readily evident that the results illustrated by the curve 72 are substantially more consistent as to the filtrate volume produced and, consequently, the fluid loss index is very consistent.

From the foregoing detailed description, it is believed evident that apparatus constructed in accordance with the invention produces repeatable tests that indicate the true fluid loss characteristics of the polymer drilling muds and eliminates the contradictions that are present when such muds were tested in the standard A.P.I. test cells. Also, the test procedures utilized in the vessel constructed in accordance with the invention yielded reproducible and consistent results which can be correlated to historical data available in fluid loss indices for drilling muds over the years. Further, close correlation can be drawn with the low temperature, low pressure test when using this system in contradistinction to the problems encountered in trying to correlate the high pressure, high temperature tests run in the standard A.P.I. cell with the standard low temperature, standard low pressure tests.

It will be apparent that the embodiment described herein has been presented by way of example only, and many changes can be made thereto without departing from the spirit or scope of the invention.

What is claimed is:

1. A method of filtration testing polymer drilling muds for fluid loss characteristics comprising the steps of:
   fastening a planar filter paper in a vertically oriented position within a test vessel, said filter paper fastened around a filtrate port in said test vessel;
   introducing the mud to be tested into said test vessel on one side of said filter paper therein;
   elevating the temperature of the mud to a predetermined value allowing weighting material in the mud to settle out of suspension;
   raising the pressure in said vessel and on said mud to apply a pressure differential of a predetermined value across said filter paper;
   passing a filtrate from said mud through said filter paper to said filtrate port in a generally horizontal flow path; and
   measuring the volume of filtrate from said mud passed through said filter paper over a predetermined time period.

2. The method of claim 1 wherein the temperature of the mud is elevated to about 250° F.–400° F.

3. The method of claim 1 wherein the temperature of the mud is elevated to the anticipated bottom hole temperature of the well in which the mud is to be used.

4. The method of claim 1 wherein the pressure differential across said filter is about 500 psi.

5. The method of claim 2 wherein the pressure differential across said filter is about 500 psi.

6. The method of claim 3 wherein the pressure differential across said filter is about 500 psi.

7. A filtration test vessel for use in the fluid loss testing of polymer drilling muds comprising:
   a pressure vessel including a generally vertically oriented side wall, a removable top, and a bottom, said pressure vessel including a filtrate port intermediate said top and bottom, said filtrate port having a horizontally oriented central axis;
   heating means for elevating the temperature of a mud;
   pressure means for raising the pressure of the mud in said pressure vessel; and
   filter means in said pressure vessel including a generally vertically oriented planar filter paper, said filter paper having a first side exposed to the mud, a second side in communication with said filtrate port, and a bottom edge located above the bottom of said pressure vessel forming a settling chamber wherein weighting materials in the mud can settle without affecting the flow area through said filter paper, said filter means including a support for maintaining said filter paper in a vertically oriented position.

8. The test vessel of claim 7 wherein said filter paper has a flow area of about seven square inches.

9. The test vessel of claim 7 wherein said heating means is located in said pressure vessel.

10. The test vessel of claim 7 where said heating means is external of said pressure vessel.

11. The test vessel of claim 7 wherein:
    said top, bottom and side wall are separate members releasably retained in sealing engagement to form said pressure vessel; and
    holding means for releasably retaining said top, bottom and sidewall assembled.

12. The test vessel of claim 8 wherein:
    said top, bottom and side wall are separate members releasably retained in sealing engagement to form said pressure vessel; and
    holding means for releasably retaining said top, bottom and sidewall assembled.

13. The test vessel of claim 9 wherein:
    said top, bottom and side wall are separate members releasably retained in sealing engagement to form said pressure vessel; and
    holding means for releasably retaining said top, bottom and sidewall assembled.

14. The test vessel of claim 7, said support comprising:
    a screen extending across said filtrate port in a vertically oriented position, said screen juxtaposed against one of said sides of said filter paper.

* * * * *